United States Patent [19]

Kitazumo et al.

[11] Patent Number: 5,189,204
[45] Date of Patent: Feb. 23, 1993

[54] OPTICAL ACTIVE 3-(2-TRIFLUORO-1-HYDROXYETHYL) PROPENYL BENZYL ETHER, DERIVATIVES THEREOF, METHOD FOR PREPARING THE SAME AND USE THEREOF FOR LIQUID CRYSTAL COMPOUND

[75] Inventors: Tomoya Kitazumo, Tokyo; Takashi Yamazaki, Kanagawa; Hitoshi Iwatsubo, Tokyo, all of Japan

[73] Assignee: Showa Shell Sekiyu Kabushiki Kaisha, Tokyo, Japan

[21] Appl. No.: 720,747

[22] Filed: Jun. 25, 1991

Related U.S. Application Data

[60] Division of Ser. No. 396,421, Aug. 21, 1989, Pat. No. 5,047,396, which is a continuation-in-part of Ser. No. 271,744, Nov. 15, 1988, abandoned.

[51] Int. Cl.$^5$ ............... C07C 67/02; C07C 69/76; C07C 41/00
[52] U.S. Cl. ............... 560/254; 560/221; 560/106; 560/8; 568/662; 568/663; 568/607
[58] Field of Search ............... 560/254, 221, 106, 8; 568/607, 663

[56] References Cited

U.S. PATENT DOCUMENTS 3,360,548 12/1967 Clark et al. ............... 560/254

FOREIGN PATENT DOCUMENTS 47909 7/1979 European Pat. Off. ............ 560/254

*Primary Examiner*—Jose G. Dees
*Assistant Examiner*—Keith MacMillan
*Attorney, Agent, or Firm*—Darby & Darby

[57] ABSTRACT

3-(2-Trifluoro-1-hydroxyethyl)propenyl benzyl ether or derivatives thereof having the formula

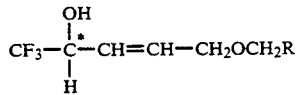

wherein R is a substituted or not substituted phenyl group and a mark * shows an asymmetric carbon atom, and derivatives thereof are provided, which are useful as a material for preparing liquid crystal compound.

3 Claims, 1 Drawing Sheet

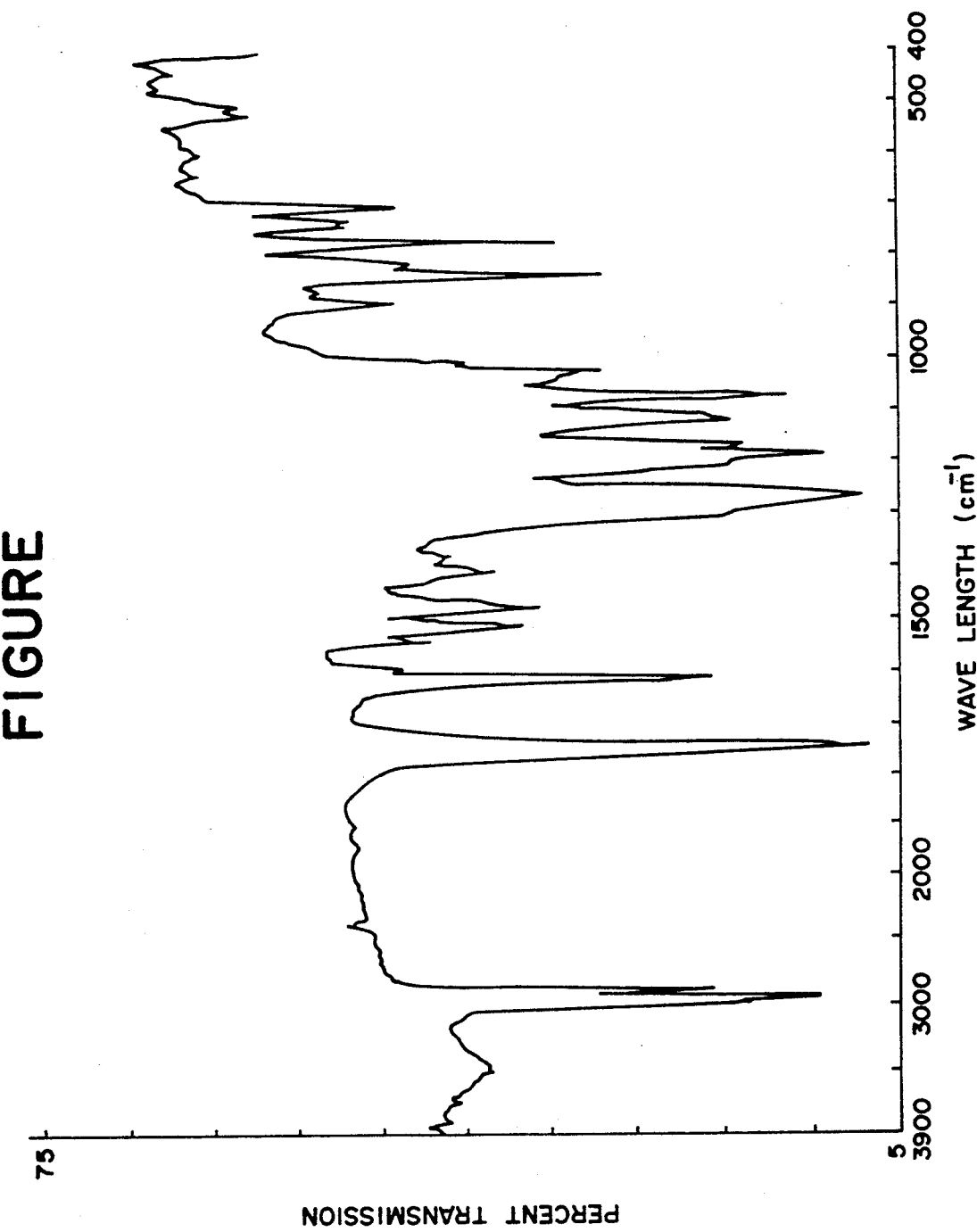

OPTICAL ACTIVE 3-(2-TRIFLUORO-1-HYDROXYETHYL) PROPENYL BENZYL ETHER, DERIVATIVES THEREOF, METHOD FOR PREPARING THE SAME AND USE THEREOF FOR LIQUID CRYSTAL COMPOUND

This is a division of application Ser. No. 396,421, filed Aug. 21, 1989, now Pat. No. 5,047,396, which is a continuation of 07/271,344, filed Nov. 15, 1988 now abandoned.

Application field of fluorine chemistry is becoming broader due to specific and unique properties of fluorine atom-containing compounds. There are many reports on bioactive materials having fluorine atoms in their molecules. In this field, an issue is mainly directed to relation between activity and molecular structure of a compound.

Synthesis of artificial organic fluorine compounds is very difficult, particularly in the case where a fluorine atom or a trifluoromethyl group is introduced to an asymmetric carbon in a molecule of a naturally produced, bioactive hydrocarbon substance.

This would possibly owe to the fact that the fluorine atom, even if only one, brings about great change in the chemical properties of a molecule. Methods familiar to the skilled in organic synthesis are hardly applied thereto without any modification.

Optical resolution of organic fluorine compounds is needed in order to use them as bioactive materials. One of the procedures to this effect is asymmetric hydrolysis. No report has been found with respect to synthesis of optically active substances by use of microorganisms through asymmetric hydrolysis of fluorine compounds, particularly trifluoromethyl group-containing compounds, although there are numerous reports on synthesis of useful optically active compounds by asymmetric hydrolysis using enzymes obtained from microorganisms or animals.

It is important to develop an economical method which is able to have fluorine atoms introduced into the desired position in a molecule, while its configuration is controlled However, so far as fluorine chemistry is concerned, neither a method for preparing both enantiomers or syn- and anti-diastereomers, controlling configuration, nor identification of absolute structure of the compound has been studied.

It is also possible to further convert an epoxy compound to a bioactive materials, said epoxy compound having been prepared by epoxidizing the organic fluorine compound synthesized. These compounds are materials for liquid crystal compounds or physiologically active compounds.

The present invention is directed to

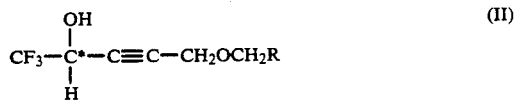

(wherein R stands for a substituted or not-substituted phenyl group)

and alkene compounds, epoxy compounds and optical isomers thereof and a process for preparing the same.

The present compounds (II)–(IX) and synthesis route thereof are shown below.

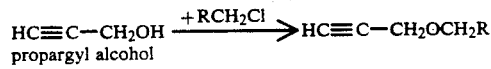

(wherein R stands for a substituted or not substituted phenyl group)

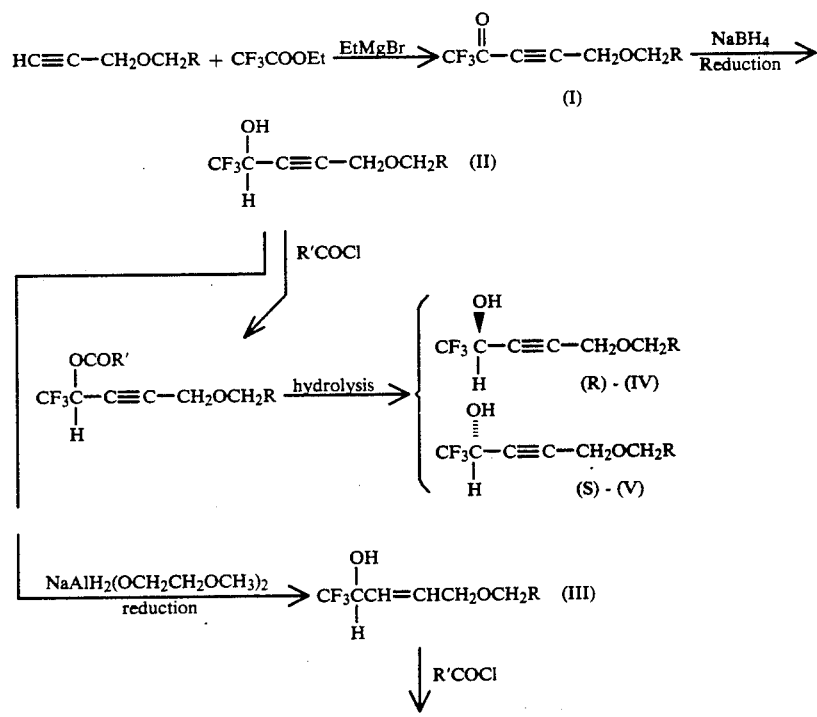

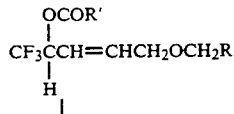

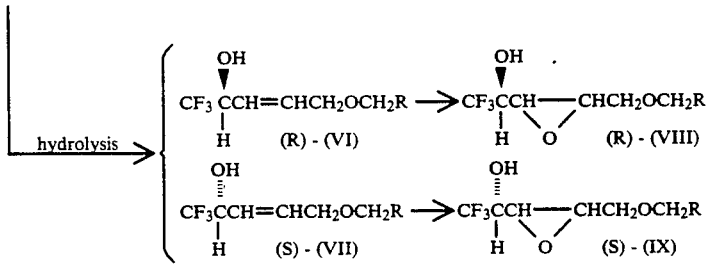

In a reaction from (I)–(II), purification of (I) is not always necessary, since (I) is ready to be decomposed in distillation.

Synthesis of racemic compound

Proparagyl alcohol and enzyl chloride are allowed to react to botain ether.

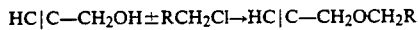

wherein R stands for a substituted or not-substituted phenyl group.

Reaction of the their above with a Grignard reagent and ethyl rifluoroacetate at low temperature gives ketone (I) having a trifluoromethyl group.

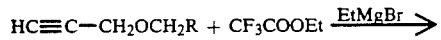

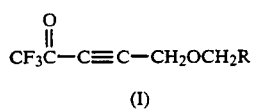

The Ketone (I) is so hardly purified that the carbonyl group thereof is subjected to reduction to convert to alcohol which is isolated and purified.

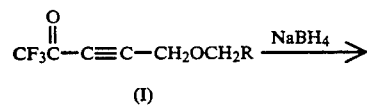

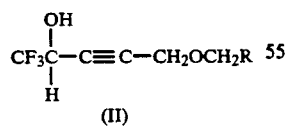

Compound (II) is allowed to react with a reducing agent such as reducing aluminum until the corresponding alkene is obtained.

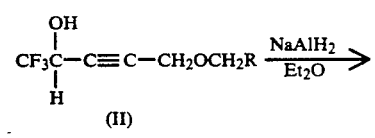

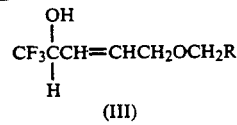

Optical resolution of compound (II)

Compound (II) is converted to acetate or isobutylate thereof and then lipase or esterase such as Lipase MY and Lipase P are added to cause asymetyric hydrolysis until optically active compounds are obtained. Lipases above and trade names of liopase available in the market, and originated from *Candida cylindracea* provided from Meito Sangyo Co., Ltd.

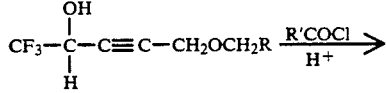

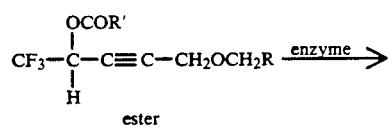

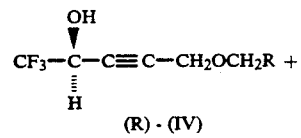

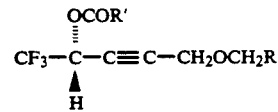

wherein R stands for a substituted or not substituted phenyl group.

As used herein, the symbol R' stands for any esterifiable organic group used in the foregoing reaction schemes.

Preferably, R' is a lower alkyl group such as $CH_3-$, $CH_3CH_2-$, $CH_3CH_2CH_2-$ and $(CH_3)_2CHCH_2-$, an arayl or an arylalkyl such as phenyl or

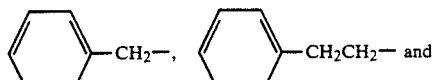

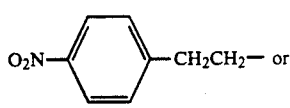

an alkenyl such as $CH_2=CHCH_2-$ and $CH_2=CHCH_2CH_2CH_2-$.

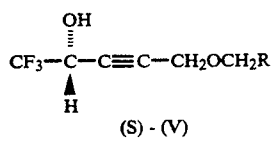

(S) - (V)

wherein R stands for a substituted or not substituted phenyl group.

Optical resolution of compound (III)

Similar to the above, compound (III) is converted to acetate or isobutylate thereof before applying lipase or esterase thereto in order to asymmetrically hydrolyze. The lipase is such as Lipase MY and Lipase P.

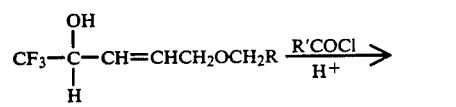

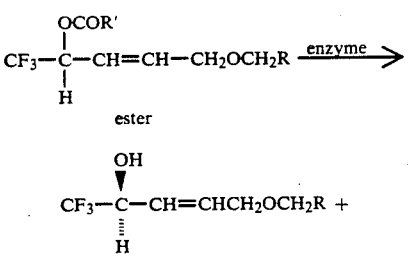

(R) - (VI)

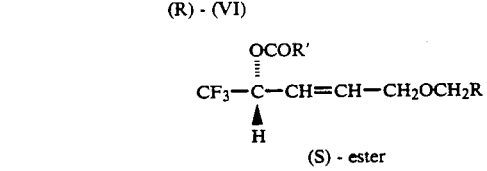

(S) - ester wherein /R stands for a substituted or not substituted phenyl group.

(S) - (VII)

wherein R stands for a substituted or not substituted phenyl group.

Expoxidation of compound (VI) or (VII)

To compound (VI) or (VII) is added organic peroxide such as meta-chloroperbenzoic acid (mCPBA) or tert.-butyl hydroperoxide (tBHP) to obtain compound (VIII) or (IX).

$$CF_3CCH=CHCH_2OCH_2R \xrightarrow{\text{mCPBA or TBHP}}_{CH_2Cl_2}$$
(VI)

(VIII)

$$CF_3CCH=CHCH_2OCH_2R \xrightarrow{\text{mCPBA or TBHP}}_{CH_2Cl_2}$$
(VII)

(IX)

The present compound having a trifluoromethyl group and a hydroxyl group is allowed to react with substituted benzoic acid to produce a liquid crystal compound having 1–4 phenylene groups and a trifluoromethyl group. The liquid crystal compound is a specific and high performance ferroelectric liquid crystal compound, since it contains one trifluoromethyl group, and has such properties that remarkable spontanious polarization, high speed of response to electric fields, chemical stability and ferroelectricity within a wide temperature range. In concrete, a liquid crystal compound is prepared by the following steps:

1. 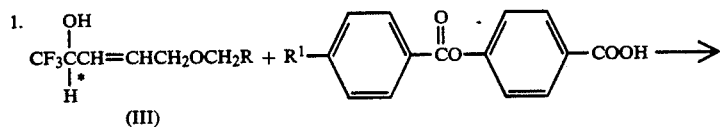

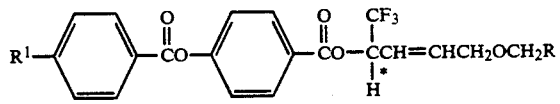

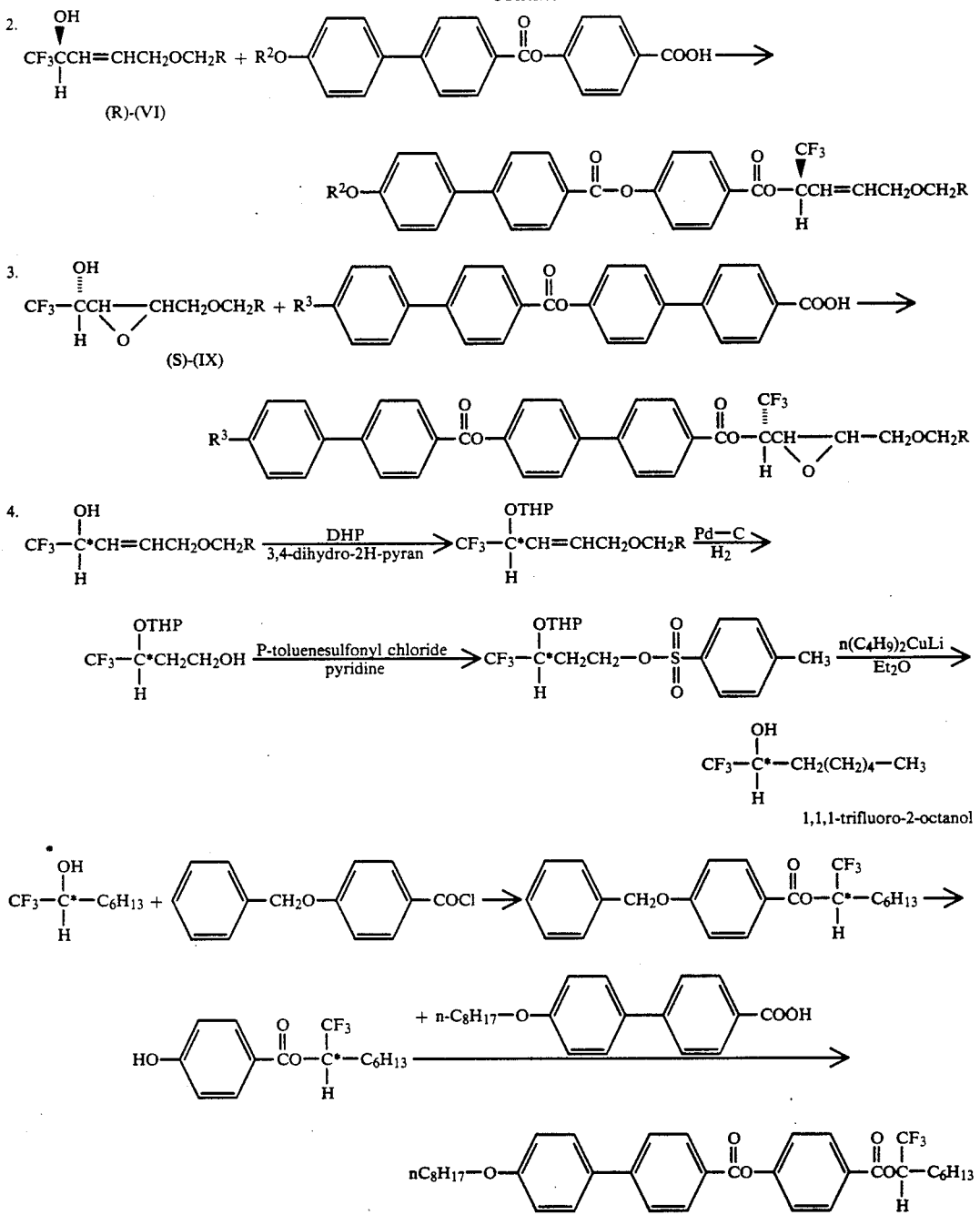

Note: THP = tetrahydroxypyranyl

EXAMPLES

Example 1

(a) Synthesis of ketone (I) Where R is phenyl

In a three-neck flask (200 ml) having a Dimroth condenser and a dropping funnel (100 ml) with a side-channel was charged magnesium (2.92 g, 120 mmol) which was then dried under reduced pressure in an argon atmosphere. Thereto were charged dried tetrahydrofuran (20 ml) and ethyl bromide (0.46 ml). As soon as reaction started, the solution of ethyl bromide (7.00 ml) in tetrahydrofuran (80 ml) was added drop by drop at a rate that gentle refluxing occurred, and the content was stirred for a further 1.5 hours. Total amount of ethyl bromide added was 7.46 ml, 100 mmol.

To the Grignard reagent thus obtained was added benzyl propargyl ether (14.62 g, 100 mmol) which had been dried under reduced pressure in an argon atmosphere and diluted with tetrahydrofuran (20 ml) and the mixture was refluxed for one hour under heating to prepare a reagent (I).

Into a three-neck flask (300 ml) having a dropping funnel (200 ml) with a side-channel were charged ethyl trifluoroacetate (18.47 g, 130 mmol) and tetrahydrofuran (50 ml), and the mixture was cooled to −78° C. To the mixture was added dropwise the reagent (I) above over 30 minutes, and the mixture was stirred for 2 hours at the same temperature as above and then for 30 minutes at 0° C.

Aqueous HCl solution (1 N) was added until a reaction solution was weakly acidic and extraction was made with methylene chloride.

An oil layer was dried over anhydrous MgSO₄ and subjected to distillation under reduced pressure to remove a low boiling point substance.

The ketone obtained has the following properties:

| b.p. 100–120° C./0.5 mm Hg. | |
|---|---|
| NMR: | |
| ¹H NMR(CCl₄) | δ4.30(s, 2H, CH₂Ph), 4.58(s, 2H, CF₃CH(OH)), 7.30(s, 5H, Ph) |
| ¹⁹F NMR(CCl₄) | δ5.92(s) |
| IR(neat) | 3000, 2850(CH₂), 2200(C≡C) 1720(C=O)cm⁻¹ |

(b) Synthesis of a compound (II) where R is phenyl

An egg-plant shaped flask (200 ml) containing sodium borohydride (1.45 g, 38.4 mmol) and absolute ethanol (50 ml) was dipped in an ice bath. A solution of ketone above without purification wherein R is a phenyl group in the formula (I) in absolute ethanol (50 ml) was added drop by drop over 30 minutes and the mixture was stirred overnight at room temperature. After ethanol was distilled under reduced pressure, saturated aqueous ammonium chloride solution was added to stop the reaction. Aqueous HCl solution(1 N) was added until the reaction solution was weakly acidic and then extraction was made with methylene chloride. The extracted material was dried over anhydrous MgSO₄ and subjected to distillation under reduced pressure to remove a low boiling point substance. A crude product thus obtained was subjected to silica gel chromatography (eluent: n-hexane/ethyl acetate=3/1) to obtain a purified compound (II) where R is phenyl. Yield (two stages, total): 84 %.

NMR: ¹H NMR(CCl₄)δ3.68(b,1H,OH),4.12(d,2H,$J_{H-H}$=1.5Hz, C≡CCH₂), 4.55(s,2H,CH₂Ph), 4.54(m,1H, CF₃CH(OH)), 7.28(s, 5H,Ph).

¹⁹F NMR(CCl₄)δ0.75(d, $J_{H-F}$=5.7Hz). IR(neat) 3400(OH), 3100, 2900,(CH₂, CH)cm⁻¹.

Example 2

Synthesis of a compound (III) where R is phenyl

Into a three neck flask (50 ml) dried enough were charged under a nitrogen atmosphere solution (2.9 ml, 10 mmol) or NaAlH₂(OCH₂CH₂OCH₃)₂ (Red-A®) in 3.2 M toluene and dried diethyl ether (10 ml). The flask was cooled in an ice bath. To the solution was added drop by drop the compound (II) where R is phenyl (1.22 g, 5.00 mmol) and the mixture was stirred for 10 minutes at that temperature and overnight at room temperature. Aqueous HCl solution (1 N) was added to stop the reaction and extraction was made with ether. The extracted solution was dried over anhydrous MgSO₄ and subjected to distillation under reduced pressure to remove the solvent. A crude product obtained was subjected to silica-gel chromatography (eluent: n-hexane/ethyl acetate: 2 / 1) to obtain the purified titled compound. Yield=80%.

NMR: ¹H NMR(CCl₄)δ3.94(bs,1H,OH),4.20(d,2H, $J_{H-H}$=5.4Hz,CH=CHCH₂), 4.47(m,1H,CF₃CH(OH)),4.73(s, 2H,CH₂Ph),6.05(dd,1H,$J_{H-H}$=5.3, 16.5Hz,CF₃CHCH=),6.37(dt, $J_{H-H}$=5.4,16.5Hz,CF₃CHCH=CH), 7.68(s,5H,Ph).

¹⁹F NMR(CCl₄)δ0.75(d, JH-F=6.6Hz). IR(neat) 3400(OH),3050,2880(CH₂,CH) 980(C=C trans)cm⁻¹.

Example 3

Optical resolution of compound (II) where R is phenyl a) Synthesis of acetate

Into a three neck flask (50 ml) very dried were charged, under a nitrogen atmosphere, methylene chloride (15 ml), compound (II) where R is phenyl (1.22 g, 5.00 mmol) and acetyl chloride (0.43 ml, 6.05 mmol). The flask was cooled in an ice bath. Thereto was added drop by drop pyridine (0.49 ml, 6.06 mmol). The flask was left to stand at room temperature and then at that temperature stirring was effected overnight. Aqueous HCl solution (1 N) was added to stop the reaction Extraction was made with methylene chloride. The extracted solution was washed with saturated aqueous sodium hydrogencarbonate solution, and dried over anhydrous MgSO₄ and then subjected to distillation under reduced pressure to remove the solvent. A crude product obtained was purified by silica-gel chromatography to obtain the titled acetate (1.281 g, 4.47 mmol). Yield: 89%.

NMR:
¹H NMR(CCl₄)δ2.17(s,3H,CH₃C(0)), 4.15(d,2H,$J_{H-H}$=1.7Hz, CeCCH₂),4.57(s,2H, CH₂Ph),5.84(m,1H, CF₃CH(OH)),7.67(s,5H, Ph).

¹⁹F NMR(CCl₄)δ−1.83(d,$J_{H-F}$=6.2Hz). IR(neat) 3050,2850(CH₂,CH), 1760(C=O)cm⁻¹.

The corresponding isobutyrate was synthesized in the similar manner to the above. Yield: 99%.

NMR: ¹H NMR(CCl₄) 61.27(d,6H,$J_{H-H}$=6 8Hz, CH₃),2.67(sep.,1H,(CH₃)₂CH), 4.15(d,2H,$J_{H-H}$=2.3Hz, C=CCH₂),4.55(s,2H, CH₂Ph),5.87(m,1H, CF₃CH(OH)),7.33(s,5H, Ph).

¹⁹F NMR(CCl₄)δ0.83(d,$J_{H-F}$=5.6Hz). IR(neat) 3000,2950(CH₃, CH₂, CH) 1760(C=O)cm⁻¹.

b) Asymmetric hydrolysis of acetate

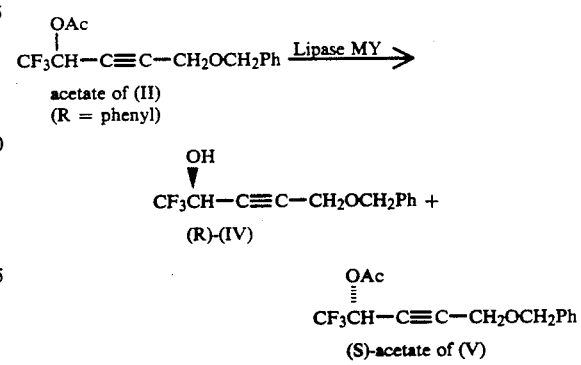

Into an egg-plant shaped flask (500 ml) were charged acetate obtained above (6.964 g, 24.3 mmol), Lipase MY (supplied from Meito Sangyo, 8.1 g, 243000 unit) and distilled water (300 ml). Stirring was made at 40°–41° C. in a thermostat. Acetic acid produced therein as the reaction proceeded was titered with aqueous NaOH solution (1 N) to watch the degree of hydrolysis. When the degree of hydrolysis reached a given value, the reaction solution was filtered on Celite. The filtrate was extracted with ethyl acetate. The solution extracted was dried over anhydrous MgSO4 and subjected to distillation under reduced pressure to remove a low boiling point substance. A crude product thus obtained was purified by silica-gel chromatography to obtain the corresponding (R)-compound (IV) where symbol R is phenyl (1.099 g, 4.50 mmol, optical purity 88% e.e., $[\alpha]_D -1.68°$ (C 1.10, MeOH)) and acetate of (S)-compound (V) where symbol R is phenyl (4.867 g, 17.0 mmol, $[\alpha]_D +16.10°$ (c 1.26 in MeOH)). Yield: 88%.

In place of Lipase MY, the similar optical resolution to the above was applied to by use of Lipase P.

The results are

| Enzyme | | Hydrolysis (%) | Optical purity |
|---|---|---|---|
| Acetate | Lipase MY | 27 | 88(R) |
| Acetate | Lipase P | 37 | 50(sd,5 S) |
| Isobutylate | Lipase MY | 31 | 40(sd,5 S) |
| Isobutylate | Lipase P | 20 | 84(sd,5 S) |

Example 4

Optical resolution of compound (III) where R is phenyl a) Synthesis of acetate

The similar manner to acetate of compound (II) was effected. To a solution of compound (III) where R is phenyl (0.985 g, 4.00 mmol) and acetyl chloride (0.34 ml, 4.80 mmol) in methylene chloride (10 ml) was added pyridine (0.39 ml, 4.80 mmol) at 0 °C. and the solution was left to stand at room temperature. After the temperature reached room temperature, the solution was stirred overnight. Aqueous HCl solution (1 N) was added to stop the reaction before extraction was made with methylene chloride. The extracted solution was washed with saturated aqueous sodium hydrogencarbonate, dried over anhydrous MgSO4 and subjected to distillation under reduced pressure to remove the solvent. A crude product obtained was purified by silica-gel chromatography to obtain the titled acetate. Yield: 76%.

NMR:

$^1$H NMR(CCl4)$\delta$2.25(s, 3H, CH3CO), 4.25(d, 2H, $J_{H-H}$=5.3Hz, CH=CHCH2), 4.75(s, 2H, CH2Ph), 6.05(dd, 1H, $J_{H-H}$=8.1, 15.6H2, CF3CHCH=), 5.96(m, 1H, CF3CH), 6.42 (dt, $J_{H-H}$=5.3, 15.6Hz, CF3CHCH=CH), 7.70(s, 5H, Ph).

$^{19}$F NMR(CCl4)$\delta$1.83(d, $J_{H-F}$=8.1Hz). IR(neat) 3050, 2900(CH2, CH), 1760 (C=O), 970(C=C trans)cm$^{-1}$.

b) Asymmetric hydrolysis of acetate

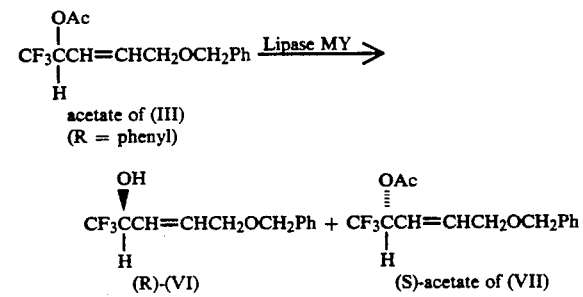

acetate of (III)
(R = phenyl)

(R)-(VI)      (S)-acetate of (VII)

Into an egg-plant shaped flask (500 ml) were charged acetate above (0.900 g, 3.00 mmol), Lipase MY (0.54 g, 16200 unit) and distilled water (30 ml). Stirring was continued at 40°–41° C. in a thermostat. Acetic acid produced therein as the reaction went on was titered with aqueous NaOH solution (1 N) to watch degree of hydrolysis.

When degree of hydrolysis reached 30%, the reaction solution was filtered on Celite. The filtrate was extracted with ethyl acetate. The solution extracted was dried over anhydrous MgSO4 and subjected to distillation under reduced pressure to remove a low boiling point substance. A crude product was purified by silica-gel chromatography to obtain the corresponding (R)-compound (VI) wherein symbol R is phenyl (0.174 g, 0.71 mmol, optical purity 88% e.e., $[\alpha]D$ 7.91° (c 1.23 in MeOH)) and acetate of (S)-compound (VII) where symbol R is phenyl (0.573 g, 1.99 mmol). Yield: 90%.

Example 5

Epoxidation of compound (VI) where R is phenyl

Into an egg plant-shaped flask (50 ml) were charged at 0 ° C. compound (R)-(VI) where symbol R is phenyl (0.493 g, 2.00 mmol), meta-chloroperbenzoic acid (0.414 g, 2.40 mmol) and methylene chloride (15 ml) and the mixture was stirred for 36 hours at room temperature. Saturated aqueous sodium sulfite solution was added to decompose excess of peroxide compounds. Extraction was made with methylene chloride. The solution extracted was dried over anhydrous MgSO4 and subjected to distillation under reduced pressure to remove the solvent. A crude product obtained was purified by silica-gel chromatography (eluant : n-hexane/ethyl acetate =3/1) to obtain the desired epoxide (VIII) wherein R is phenyl. Yield: 67%. Diastereomer ratio was 45 : 55 on the basis of ratio of integrated areas of peaks which appeared in low and high magnetic fields, respectively, at $^{19}$F NMR.

b) Epoxidation by t-butyl hydroperoxide

In an egg plant-shaped flask, t-butyl hydroperoxide (3.2 mmol) in benzene (1.1 ml) and vanadium oxide acetylacetonate (8 mg, 0.11 mmol) were added to the solution of (R)-(VI) where symbol R is phenyl (0.746 g, 3.03 mmol) in methylene chloride (20 ml). The mixture was stirred at room temperature overnight. Thereto was added saturated aqueous sodium sulfite solution to decompose an excess of peroxide compounds. Extraction was made with methylene chloride. The solution extracted was dried over anhydrous MgSO4 and subjected to distillation under reduced pressure to remove the solvent. A crude product was purified by silica-gel chromatography (eluant: n-hexane/ethyl acetate =3/1) to obtain the desired epoxide. Yield: 50%. Conversion: 78%. Diastereomer ratio was 71 : 29 on the basis of ratio of integrated areas of peaks which appeared in low and high magnetic fields at $^{19}$F NMR.

$^1$H NMR(CCl4)$\delta$3.00–4.17(m,6H,CF3CH,OH CH-CH-CH2OCH2Ph),4.45(s, 2H,CH2Ph),7.28(s,5H,Ph).

$^{19}$F NMR(CCl4)$\delta$0.58(d, $J_{H-F}$=6.0Hz). −0.92(d, $J_{H-F}$=5.7Hz).

IR(neat) 3450(OH), 1500(Ph), 1280 cm$^{-1}$.

Example 6

Epoxidation of compound (VII)

Example 5 was repeated to compound (S)-(VII) where R is phenyl to obtain compound (IX).

Example 7

(1) Protection of a hydroxyl group of 5-benzyloxy-1,1,1-trifluoro-3-pentene-2-ol To a solution of 5-benzyloxy-1,1,1-trifluoro-3-pentene-2-ol (10 mmol) in anhydrous diethyl ether (20 ml) were added dihydropyran (16 mmol) and a catalytic amount of p-toluenesulfonic acid, in this order. The mixture was stirred for five hours and then thereto was added saturated aqueous sodium hydrogen carbonate solution. Diethyl ether was added to effect extraction. The extract was dried and then distilled to remove the solvent. The extract obtained was used as it was for the next step (2).

(2) Synthesis of 1,1,1-trifluoro-2-tetrahydroxypyranyloxypentene

The product obtained (1) above and palladium carbon (0.2 g) were added to ethanol and the mixture was stirred for six hours at room temperature in a hydrogen atmosphere. The palladium carbon was removed by filtration. The filtrate was distilled to remove the ethanol, and then subjected to silica gel chromatography to effect separation and purification. Yield of the titled compound: 8.6 mmol.

(3) 1,1,1-Trifluoro-2-tetrahydroxypyranyloxy-pentyl p-toluenesulfonate

To a solution of the product of (2) above in methylene chloride (20 ml) were added pyridine (2.4 ml) and a solution of tosyl chloride (9.5 mmol) in methylene chloride (10 ml). The mixture was stirred overnight. Saturated sodium hydrogencarbonate was added to cease the reaction and diethyl ether was added to effect extraction. After being dried and distilled to remove the solvent, the extract was subjected to silica gel chromatography. Yield of the titled compound 6.9 mmol.

(4) Synthesis of 1,1,1-trifluoro-2-octanol

Diethyl ether (30 ml) and Li (36 mmol) were charged in a reactor under an Ar gas stream and kept at $-10°$ C. A solution of butyl bromide (17 mmol) in diethyl ether (6 ml) was gradually added to prepare $C_4H_9Li$. CuI (18 mmol) and diethyl ether (30 ml) were charged in the reactor and the reactor was kept at $-30°$ C. $C_4H_9Li$ solution obtained above was added gradually, and then the mixture was stirred for one hour. The solution was cooled to $-70°$ C. and thereto was gradually added a solution of the product of (3) above (6.9 mmol) in diethyl ether (30 ml). After the solution was left to stand overnight, 3% aqueous HCl solution and then diethyl ether were added to effect extraction. To the extract was added p-toluene sulfonic acid to effect de-protection and was subjected to silica-gel chromatography to obtain the titled compound (4.8 mmol).

Example 8

(1) Synthesis of 1,1,1-trifluoro-2-octyl-4-benzyloxybenzoate

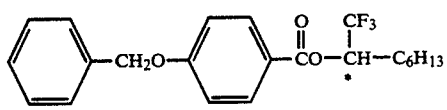

To a solution of 4-benzyloxybenzoic acid chloride (4.3 g) in methylene chloride (50 ml) was added drop by drop under ice cooling a solution of optically active 1,1,1-trifluoro-2-octanol (2.9 g), dimethylaminopyridine (0.6 g) and triethylamine (1.7g) in methylene chloride (50 ml). The solution obtained was left to stand until it reached a room temperature and left to stand overnight. The solution was poured in ice-water and methylene chloride was added thereto. The methylene chloride phase was washed with dilute hydrochloric acid, water, 1N aqueous sodium carbonate solution and water in order and dried over anhydrous magnesium sulfate. Solvent was distilled off to obtain a crude product which was treated by toluene-silica-gel chromatography and then recrystallized with ethanol to obtain the titled compound (3.8 g).

(2) Synthesis of 1,1,1-trifluoro-2-octyl-4-hydroxybenzoate

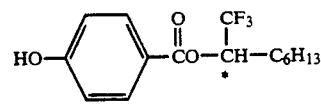

To a solution of the compound obtained in (1) above in methanol (100 ml) was added Pd (10%) carried on carbon (0.4 g), and hydrogenation was effected in the hydrogen atmosphere, to obtain the titled compound (2.8 g).

(3) Synthesis of 4-(1,1,1-trifluoro-2-octyloxycarbonyl)-phenyl-4'-n-octyloxybiphenyl-4-carboxylate

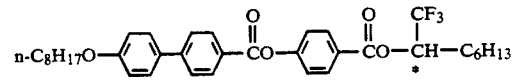

4-n-Octyloxydiphenylcarboxylic acid (3.0 g) with excess thionyl chloride were heated for six hours under refluxing. Distillation of unaltered thionyl chloride gave 4-n-octyloxydiphenylcarboxylic acid chloride.

To a solution of the acid chloride above in methylene chloride (50 ml) was gradually added under ice-cooling a solution of 1,1,1-trifluorooctyl-4-hydroxybenzoate above in (2) (2.8 g), triethyl amine (1.0 g) and dimethyl aminopyridine (0.3 9) in methylene chloride (50 ml), and the solution was left to stand overnight. The solution was poured in ice-water and methylene chloride was added. The methylene chloride layer was washed by dilute hydrochloric acid, water, aqueous sodium carbonate solution and water, in order, and was dried over anhydrous sodium sulfate. Solvent was distilled to give a crude product which was subjected to toluene-silica-gel chromatography to obtain optically active compound of the titled compound (2.1 g).

The crude compound was re-crystallized from anhydrous ethanol and phase-transition was observed.

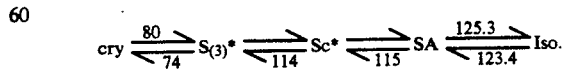

BRIEF DESCRIPTION OF THE FIGURE

Figure attached shows IR chart of this compound.

We claim:

1. Optically active alcohol of the formula:

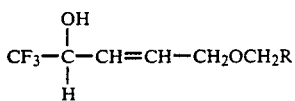 (R)-(VI)

wherein R stands for a phenyl or substituted phenyl group.

2. An ester of an optically active alcohol having the formula:

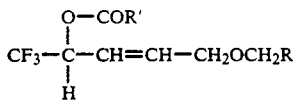 (S)-(VII)

wherein R stands for a phenyl or substituted phenyl group and R' stands for a lower alkyl, aryl, arylalkyl or alkenyl group.

3. An ester of an optically active alcohol according to claim 2 wherein R' is a member selected from the group consisting of methyl, ethyl, n-propyl, isopropyl, phenyl and p-nitrophenylethyl.

* * * * *